United States Patent
Behera

(10) Patent No.: US 10,905,454 B2
(45) Date of Patent: Feb. 2, 2021

(54) SURGICAL DEVICE

(71) Applicant: Santosh Kumar Behera, San Jose, CA (US)

(72) Inventor: Santosh Kumar Behera, San Jose, CA (US)

(*) Notice: Subject to any disclaimer, the term of this patent is extended or adjusted under 35 U.S.C. 154(b) by 351 days.

(21) Appl. No.: 16/158,678

(22) Filed: Oct. 12, 2018

(65) Prior Publication Data
US 2020/0113593 A1 Apr. 16, 2020

(51) Int. Cl.
*A61B 17/32* (2006.01)
*A61B 17/00* (2006.01)

(52) U.S. Cl.
CPC ........... *A61B 17/32002* (2013.01); *A61B 17/320068* (2013.01); *A61B 2017/0011* (2013.01); *A61B 2017/320028* (2013.01); *A61B 2017/320032* (2013.01); *A61B 2017/320064* (2013.01)

(58) Field of Classification Search
CPC ...... A61B 17/32002; A61B 17/320068; A61B 17/22012; A61B 17/320783; A61B 2017/320064; A61B 2017/00318; A61B 2017/320028; A61B 2017/00402; A61B 34/76; A61B 2017/0011; A61B 2017/22079; A61B 2017/320032; A61B 2017/00345
See application file for complete search history.

(56) References Cited

U.S. PATENT DOCUMENTS

| | | | |
|---|---|---|---|
| 5,728,089 A * | 3/1998 | Lal ..................... | A61B 18/1402 606/1 |
| 6,214,017 B1 * | 4/2001 | Stoddard ........ | A61B 17/320068 606/128 |
| 6,494,882 B1 * | 12/2002 | Lebouitz ................ | A61B 17/32 606/45 |
| 6,638,249 B1 * | 10/2003 | Lal ..................... | A61B 5/14514 604/151 |
| 6,764,308 B1 | 7/2004 | Broberg et al. | |
| 6,923,790 B2 * | 8/2005 | Lal ..................... | A61B 5/14514 128/200.16 |
| 10,398,596 B2 * | 9/2019 | Hunter ................ | A61F 9/00745 |
| 2002/0193817 A1 * | 12/2002 | Lal ..................... | A61F 9/00745 606/169 |
| 2004/0193198 A1 * | 9/2004 | Cuny ............. | A61B 17/320068 606/169 |
| 2005/0154255 A1 | 7/2005 | Jacobs | |
| 2007/0010802 A1 | 1/2007 | Despres | |
| 2007/0129743 A1 | 6/2007 | Cagle | |
| 2009/0095790 A1 | 4/2009 | Whitman et al. | |

(Continued)

*Primary Examiner* — Phong Son H Dang
(74) *Attorney, Agent, or Firm* — Kanika Radhakrishnan; Evergreen Valley Law Group

(57) ABSTRACT

Disclosed is a surgical device. The surgical device includes a housing. The surgical device also includes a linear actuator disposed in the housing. The linear actuator includes a central rod. The linear actuator also includes one or more bending modules connected to the central rod. Each of the one or more bending modules includes one or more bending actuators. Each of the one or more bending actuators includes one or more layers of piezoelectric bending elements configured to provide a reciprocating movement to the central rod upon application of a voltage. The surgical device further includes a cutting mechanism coupled to the central rod.

18 Claims, 9 Drawing Sheets

(56) References Cited

U.S. PATENT DOCUMENTS

| | | | |
|---|---|---|---|
| 2011/0130664 A1* | 6/2011 | Nakagawa | A61C 17/20 600/459 |
| 2011/0137330 A1* | 6/2011 | Moreau-Gaudry | A61B 17/00234 606/167 |
| 2014/0135663 A1* | 5/2014 | Funakubo | A61B 17/320068 601/2 |
| 2017/0151012 A1 | 6/2017 | Griffiths et al. | |
| 2017/0290602 A1* | 10/2017 | Germain | A61B 34/74 |
| 2018/0056095 A1* | 3/2018 | Messerly | A61N 7/02 |

* cited by examiner

SURGICAL DEVICE

TECHNICAL FIELD

The present disclosure relates generally to surgical devices and, more particularly to, a tissue resection device capable of in-situ stiffness differentiation for surgical procedures.

BACKGROUND

Certain surgical procedures require removal of malignant tumors or tissues without damaging the healthy tissues. This becomes especially critical in neurosurgery where small errors can have devastating consequences. In spite of recent advances in MEMS (Micro-Electro-Mechanical Systems) devices and miniaturization of technology, there is a growing need for precise minimally invasive tissue resection devices that can transfer the cutting forces through a tiny opening. Another area of considerable research focus over the past few years is haptic feedback in minimally invasive surgery. Lack of haptic feedback is a limiting factor in the successful and widespread adoption of many surgical devices. Tissue stiffness estimation and differentiation is a crucial aspect of haptics that can provide a surgeon with useful information in the absence of conventional methods of tissue differentiation such as palpation by hand.

To overcome the lack of physical palpation in minimally invasive surgical (MIS) procedures, the ability to distinguish between different tissue types in-situ would be highly beneficial to surgeons. Even though there are numerous stand-alone devices for tissue resection as well as standalone sensing devices known in the art, there is no known device that combines the two functions to provide a self-sensing tissue resection device. Combining tissue resection with self-sensing ability in actuator itself, which can be leveraged for differentiating between tissues based on their stiffness values, would result in significant time savings that would otherwise have been spent in swapping devices to do the two tasks. Reducing surgery time is beneficial not only for the surgeons (less fatigue) but also for the hospitals since operating room time is one of the most expensive variables in a surgery.

Furthermore, MIS procedures require miniaturization of devices so that they can fit through a small opening. In this context the challenge is to transmit the forces and moments generated by the actuator to end effector through a compact and reliable mechanism. Conventionally surgical devices utilize actuators that have been based on magnetic effect like solenoids or have used a mechanism to convert rotary motion of a DC motor into linear motion like the lead screw mechanism or a cam arrangement. Such actuating mechanisms utilize friction to achieve corresponding linear motion which makes them generally inefficient, and also usually require relatively large space which makes it difficult to incorporate such actuating mechanism in a small enough device to be implemented for MIS procedures.

From the above discussion it may be understood that there are a few shortcomings of existing surgical devices. Towards this end, there exists a need to overcome the aforementioned limitations and develop a surgical device capable of tissue resection by providing oscillatory motion up to a few kHz with displacement in the millimeter range while providing in-situ stiffness differentiation.

SUMMARY

Various embodiments of the present disclosure provide surgical devices.

In one aspect, a surgical device is disclosed. The surgical device includes a housing. The surgical device also includes a linear actuator disposed in the housing. The linear actuator includes a central rod. The linear actuator also includes one or more bending modules connected to the central rod. Each of the one or more bending modules includes one or more bending actuators. Each of the one or more bending actuators includes one or more layers of piezoelectric bending elements configured to provide a reciprocating movement to the central rod upon applying a voltage. The surgical device further includes a cutting mechanism coupled to the central rod.

In another aspect, a surgical device is disclosed. The surgical device includes a housing. The surgical device also includes a linear actuator disposed in the housing. The linear actuator includes a central rod. The linear actuator also includes one or more bending modules connected to the central rod. Each of the one or more bending modules includes one or more bending actuators. At least one of the one or more bending actuators includes at least two layers of bending elements and a metallic layer disposed between each of the at least two layers of bending elements. The surgical device further includes a cutting mechanism coupled to the central rod.

Other aspects and example embodiments are provided in the drawings and the detailed description that follows.

BRIEF DESCRIPTION OF THE FIGURES

For a more complete understanding of example embodiments of the present technology, reference is now made to the following descriptions taken in connection with the accompanying drawings in which.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details.

Reference in this specification to "one embodiment" or "an embodiment" means that a particular feature, structure, or characteristic described in connection with the embodiment is included in at least one embodiment of the present disclosure. The appearance of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Figure 1:
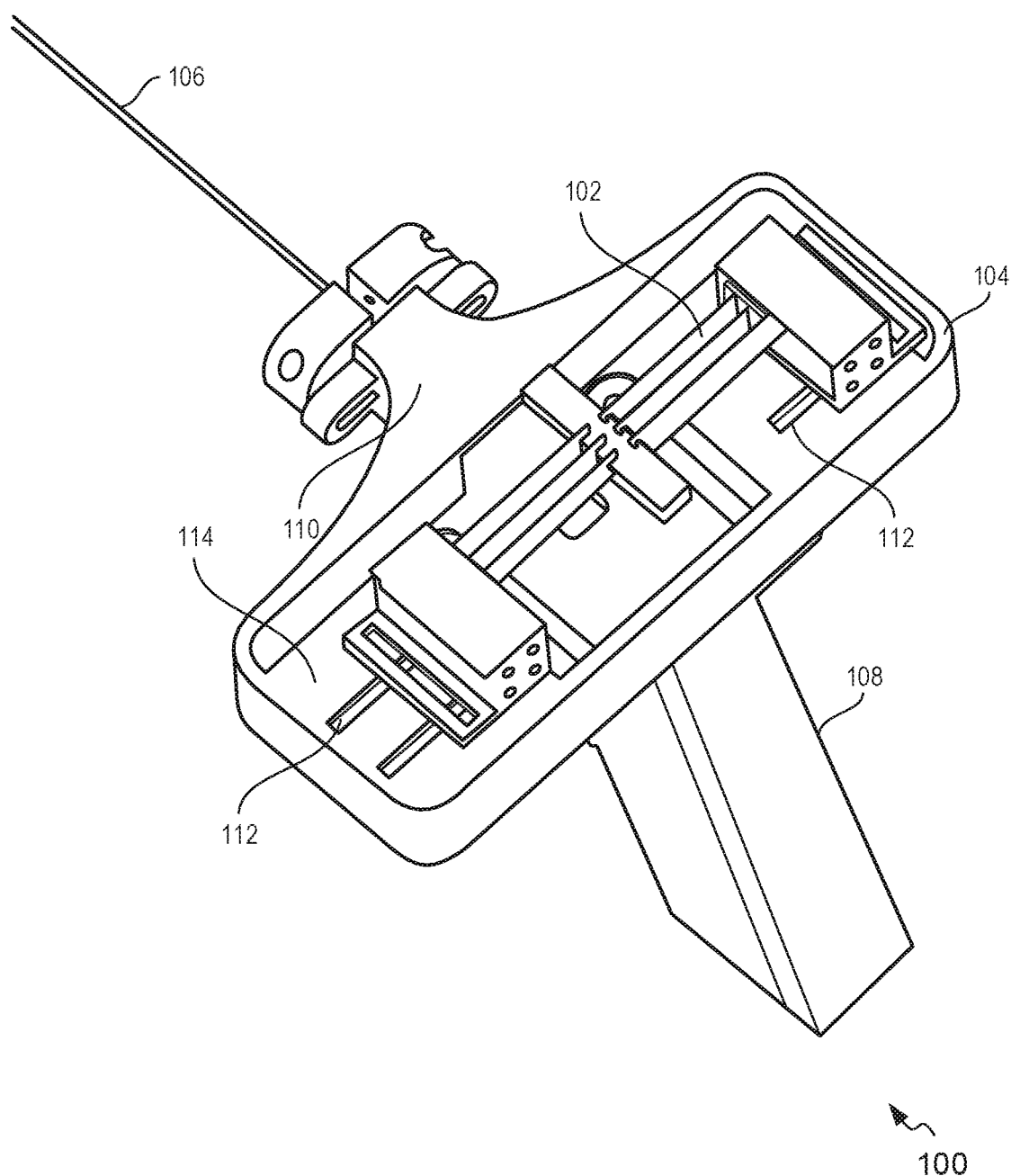
FIG. 1 is a perspective view of a surgical device with a top cover removed, in accordance with an example embodiment.

Referring to the drawings, FIG. 1 illustrates a perspective view of a surgical device 100 with a top cover (not shown) removed for showing its internal components, in accordance with an example embodiment. The surgical device 100 of the present disclosure is implemented for tissue resection and in-situ stiffness differentiation. The surgical device 100 has self-sensing capabilities which enables the present surgical device 100 to differentiate between tissues of different stiffness values in-situ, without the need of an external sensor. As illustrated in FIG. 1, the present surgical device 100 generally includes a linear actuator 102, a housing 104 to accommodate the linear actuator 102, a cutting mechanism 106 mechanically connected to the linear actuator 102 and disposed generally outside of the housing 104, and a handle 108 attached to the housing 104 for allowing a user to grasp the surgical device 100 during application or otherwise.

Figure 2:
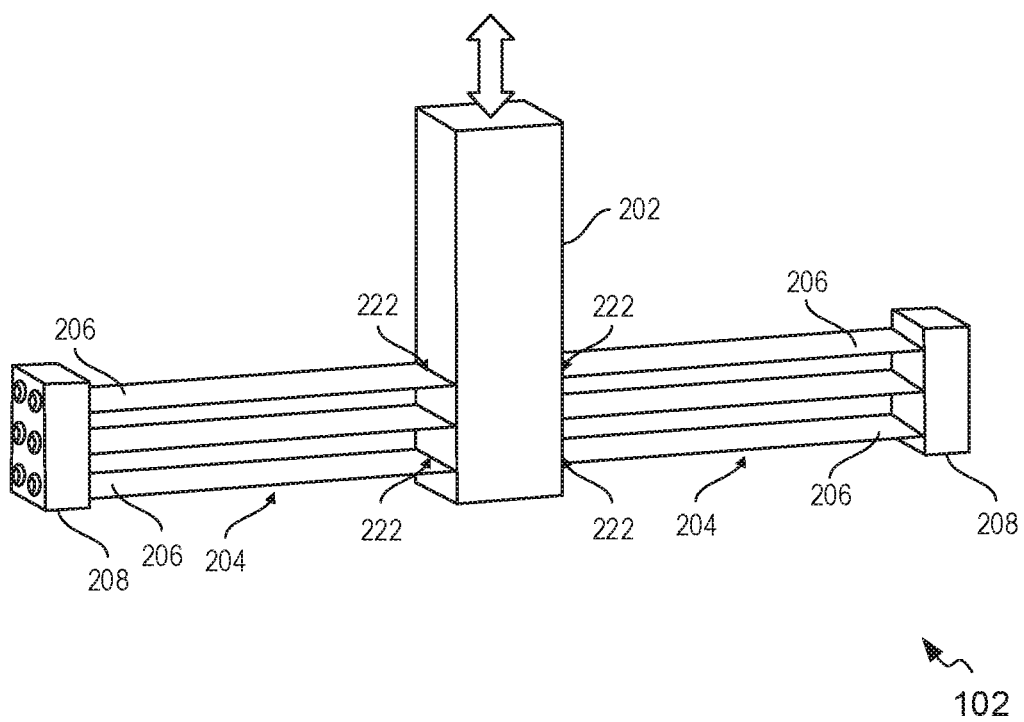
FIG. 2 is a diagrammatic view of a linear actuator for the surgical device, in accordance with an example embodiment.

FIG. 2 illustrates a perspective view of the linear actuator 102, in accordance with an embodiment of the present disclosure. The linear actuator 102, generally, includes a central rod 202 and one or more bending modules 204 coupled to the central rod 202. In the exemplary embodiment of FIG. 2, the linear actuator 102 is shown to include two bending modules 204 therein. It may be understood that the linear actuator 102 may include any number of bending modules 202 depending on the requirements of the surgical device 100, as will be discussed in more detail in the subsequent paragraphs. In the linear actuator 102, the bending modules 204 may be disposed co-axially about the central rod 202.

Figure 3:
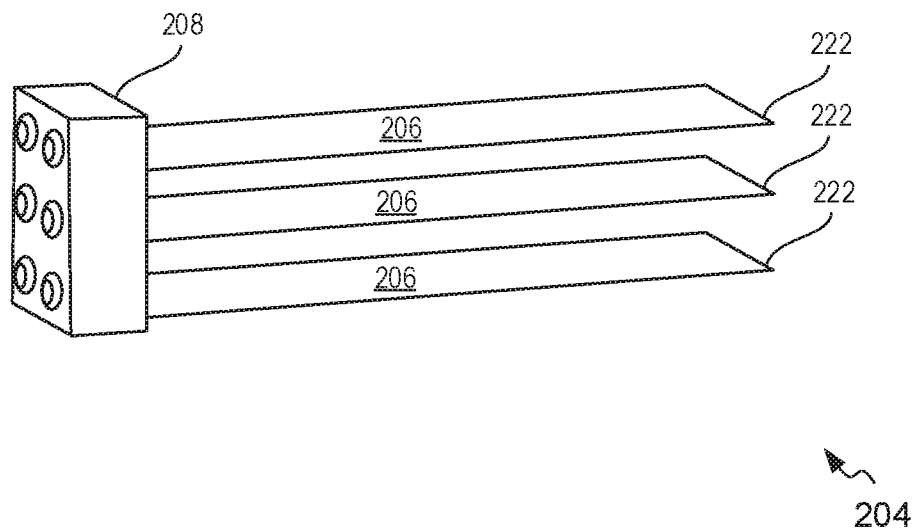
FIG. 3 is a diagrammatic view of a bending module of the linear actuator, in accordance with another example embodiment.

FIG. 3 illustrates a perspective view of the bending module 204 utilized in the linear actuator 102 of the present disclosure in an unassembled state, in accordance with an example embodiment. In an embodiment, each bending module 204 includes one or more bending actuators 206 supported on a support body 208 therein. In the illustration of FIG. 3, the exemplary bending module 204 is shown to include three bending actuators 206; however, it may be understood that the number of bending actuators 206 may vary based on the desired application. Further, as shown in the illustrated example, the bending actuators 206 are cantilevered on the support body 208, i.e. the one or more bending actuators 206 are supported in the form of a cantilever beam disposed one above the other. It may be contemplated that the support body 208 is formed as a unitary structure supporting the multiple bending actuators 206 thereon. The support body 208 may be constructed of any suitable insulating material, such as, but not limited to, plastic, fiberglass, asbestos, Teflon®, rubber, or any other electrically insulating polymer including polyurethane, polystyrene, etc. Although, the support body 208 is shown to have a generally cuboidal shape, it may be understood that the support body 208 may have any other suitable shape adapted for supporting the bending actuators 206, without any limitations.

Figure 4:
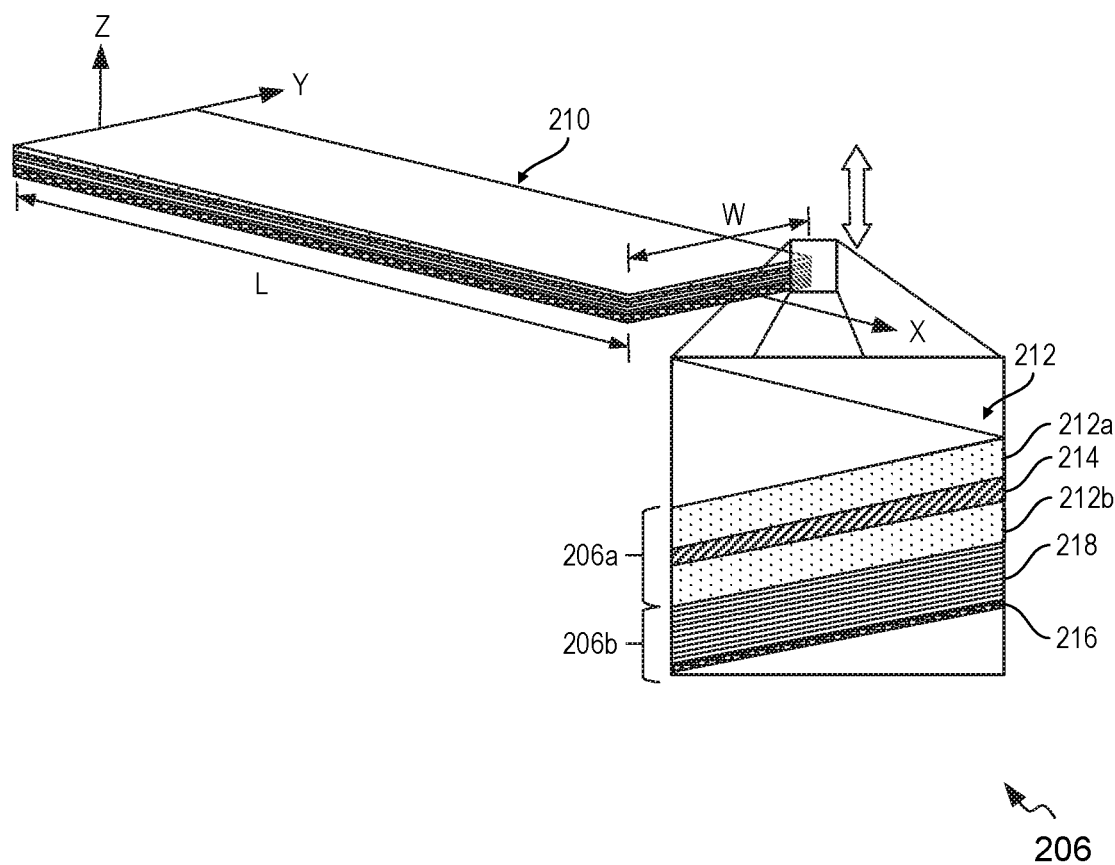
FIG. 4 is a diagrammatic view of a bending actuator of the bending module, in accordance with an example embodiment.

FIG. 4 illustrates a detailed configuration of the bending actuator 206. In an embodiment, each of the bending actuator 206 is a piezoelectric actuator. In some examples, each of the bending actuator 206 is a self-sensing piezoelectric actuator. As illustrated in FIG. 4, each of the bending actuator 206 includes a stack of layers 210 having one or more bending elements 212, and a metallic layer 214 disposed between the bending elements 212 for providing support and electrical contact therebetween. Further, in some examples, the bending actuator 206 may include a sensing element 216 disposed over one of the bending element 212, and an insulating layer 218 separating the sensing element 216 from the immediate bending element 212. In the present example, the bending elements 212 and the metallic layer 214 therebetween define an actuator portion 206a of the self-sensing bending actuator 206, and the sensing element 216 herein along with the insulating layer 218 define a sensing portion 206b of the self-sensing bending actuator 206, and such combination of the actuator portion 206a and the sensing portion 206b within the single unit configures the present bending actuator 206 to be a self-sensing bending actuator.

In some embodiments, the bending actuator 206 is a 5-layered self-sensing actuator including two layers of the bending elements 212 (bimorph structure), as illustrated in FIG. 4. In other embodiments, the bending actuator 206 may include only one layer of the bending element 212 or have more than two layers of the bending elements 212, without departing from the scope of the present disclosure. In FIG. 4, the actuator portion 206a of the bending actuator 206 has been shown to include two layers of the bending elements 212, a first bending element 212a (positioned at top) and a second bending element 212b (positioned lower). Each of the one or more bending elements 212 is a smart material beam that bends in response to an applied electrical signal. In the present embodiment, the bending elements 212 are piezoelectric bending elements. Although the bending actuator 206 has been described in terms of using piezoelectric layers as the bending elements 212, it may be contemplated by a person skilled in the art that, in alternate embodiments, the bending actuator 206 may be realized with any other smart material, such as, but not limited to, magnetostrictive or shape memory materials.

In an embodiment, the bending elements 212 are constructed of PZT-5H material (where PZT stands for lead zirconate titanate). PZT-5H is chosen as the actuator material due to its high piezoelectric coefficient, so that the bending element 212 provides a large bending or tip displacement as well as blocked force. Herein, the blocked force is defined as the maximum force output of a bending piezoelectric actuator at a given voltage when the displacement is completely blocked. Further, ease of availability as well as low price of PZT-5H compared to other commercial piezoelectric materials makes it a suitable choice. Alternatively, the bending elements 212 may be composed of any appropriate material such as lead magnesium niobate-lead titanate solid solutions, strontium lead titanate, quartz silica, piezoelectric ceramic lead zirconate and titanate (PZT), piezoceramic-polymer fiber composites, and the like. Further, the metallic layer 214 is composed of brass material. Brass is chosen primarily because of its relatively good electrical conductivity for providing electrical contact between the two bending elements 212a, 212b, and low stiffness for allowing maximum displacement of the bending actuator 206, and further for its ability to be formed into thin sheets. Further, the sensing element 216 is constructed of polyvinylidene fluoride, or polyvinylidene difluoride, (PVDF) material. PVDF is chosen for the sensing element 216 due to its high sensing resolution, ability to be formed into micrometer-sized thin sheets and low stiffness so that it offers as little resistance as possible to the motion induced by the bending elements 212. Further, the insulating layer 218 is composed of Kapton® layer which is placed between the second bending element 212b and the sensing element 216. Kapton is a polyimide film with the chemical name poly (4,4'-oxydiphenylene-pyromellitimide), and with its good dielectric qualities, large range of temperature stability and its availability as thin sheets have made it a preferred material for use as insulating material in the present configuration. In one embodiment, the metallic layer 214, the sensing element 216 and the insulating layer 218 have relatively lower elastic stiffness compared to the layers of the bending elements 212. Further, layers of adhesive compositions may be employed to adhere the various layers with each other. It may be understood that the mentioned materials for various layers 210 are preferred materials for the bending actuator 206; however, these materials may be replaced with other suitable materials of substantially similar properties and thus shall not be construed as limiting to the present disclosure.

In the bending actuator 206, the two bending elements 212a, 212b act as the actuator layers and are responsible for generating a displacement as well as force output on the application of an electric potential. For this purpose, the two bending elements 212a, 212b are connected via an electric circuit (not shown). Specifically, in the electric circuit, the two outer surfaces of the bending elements 212a, 212b are connected together electrically via a conductive wire or the like. Also, the inner surfaces of the two bending elements 212a, 212b are already disposed in electrical contact via the metallic layer 214. For example, a pair of wire leads are attached to the metallic layer 214 and to at least one of the outer surfaces of the bending elements 212a, 212b in order to provide the potential difference between the two surfaces of the corresponding bending elements 212a, 212b. To actuate the bending actuator 206, a voltage is applied to these wire leads which results in a same voltage being applied across each of the two bending elements 212a, 212b. It may be contemplated that the electrical signal is generated by a computer or a function generator and is fed to the two bending elements 212a, 212b after amplification.

Further, in the bending actuator 206, the two bending elements 212a, 212b are polarized in the same direction. Each of the bending elements 212a, 212b has orthotropic symmetry with respect to its material properties such that the material properties are the same along X and Y directions and different along Z direction. The bending elements 212a, 212b are polarized in the thickness direction, i.e. along the Z direction. When a voltage is applied across the thickness direction of each layer, it either expands or contracts. In the electric circuit, the wiring is done such that the inner surfaces of the two bending elements 212a, 212b are at a same first potential while the outer surfaces are at a same second potential. This ensures that the field directions are opposite to each other in the two bending elements 212a, 212b. When a positive voltage is applied, the electric field is aligned with the direction of polarization with the first bending element 212a whereas the electric field and polarization are in opposite directions for the second bending element 212b. This causes the first bending element 212a to expand and the second bending element 212b to contract resulting in a bending or up-down movement of the bending actuator 206 about a tip 222 of the overall assembly of the bending actuator 206, along the Z direction (as shown by means of a double-sided arrow in FIG. 4).

As seen in FIG. 2, the various bending modules 204 are connected to the central rod 202 in a manner such that the corresponding tips 222 of the one or more bending actuators 206 in each of the bending modules 204 are fixedly coupled to the central rod 202 therein. In other words, the tips 222 of all the bending actuators 206 in the bending modules 204 are fixedly coupled to the central rod 202, which acts as the end effector in the linear actuator 102. In accordance with an exemplary embodiment, the central rod 202 may be made of an insulating material, such as, for example, ABS (Acrylonitrile Butadiene Styrene) plastic. Further, the linear actuator 102 may include a thin sheet of rubber or the like between the tips 222 of the bending actuators 206 and the central rod 202. As discussed, on application of the electric potential, the bending actuators 206 may generate a bending displacement at the corresponding tips 222. And, since the bending modules 204 are arranged symmetrically in the horizontal plane orthogonal to the central rod 202, the bending movement of the bending actuators 206 may cause the central rod 202 to move to and fro in a transverse direction (as shown by means of double-sided arrows in FIG. 2).

Figure 5:
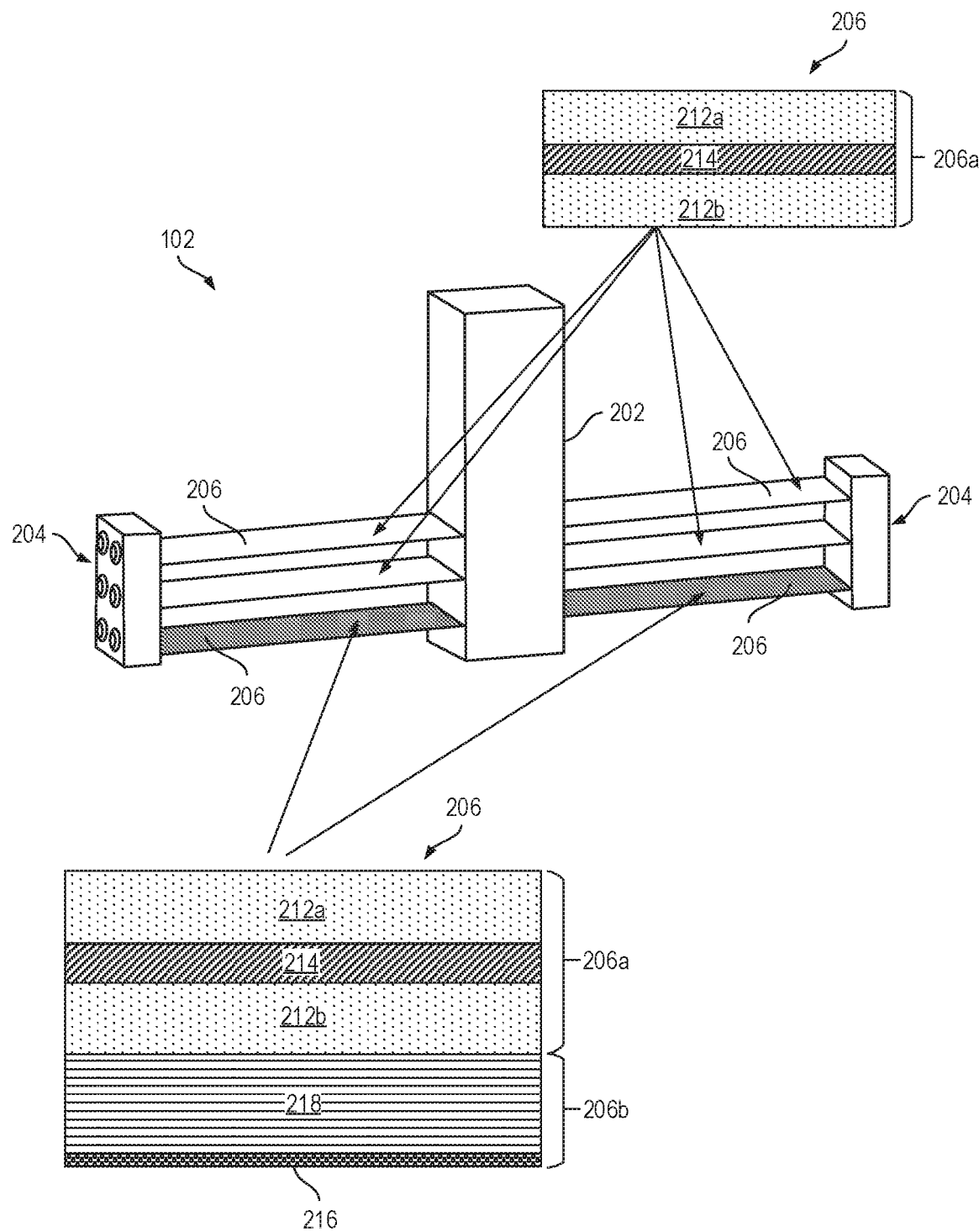
FIG. 5 is a diagrammatic view of the linear actuator for the surgical device, in accordance with a first example embodiment.
Figure 6:
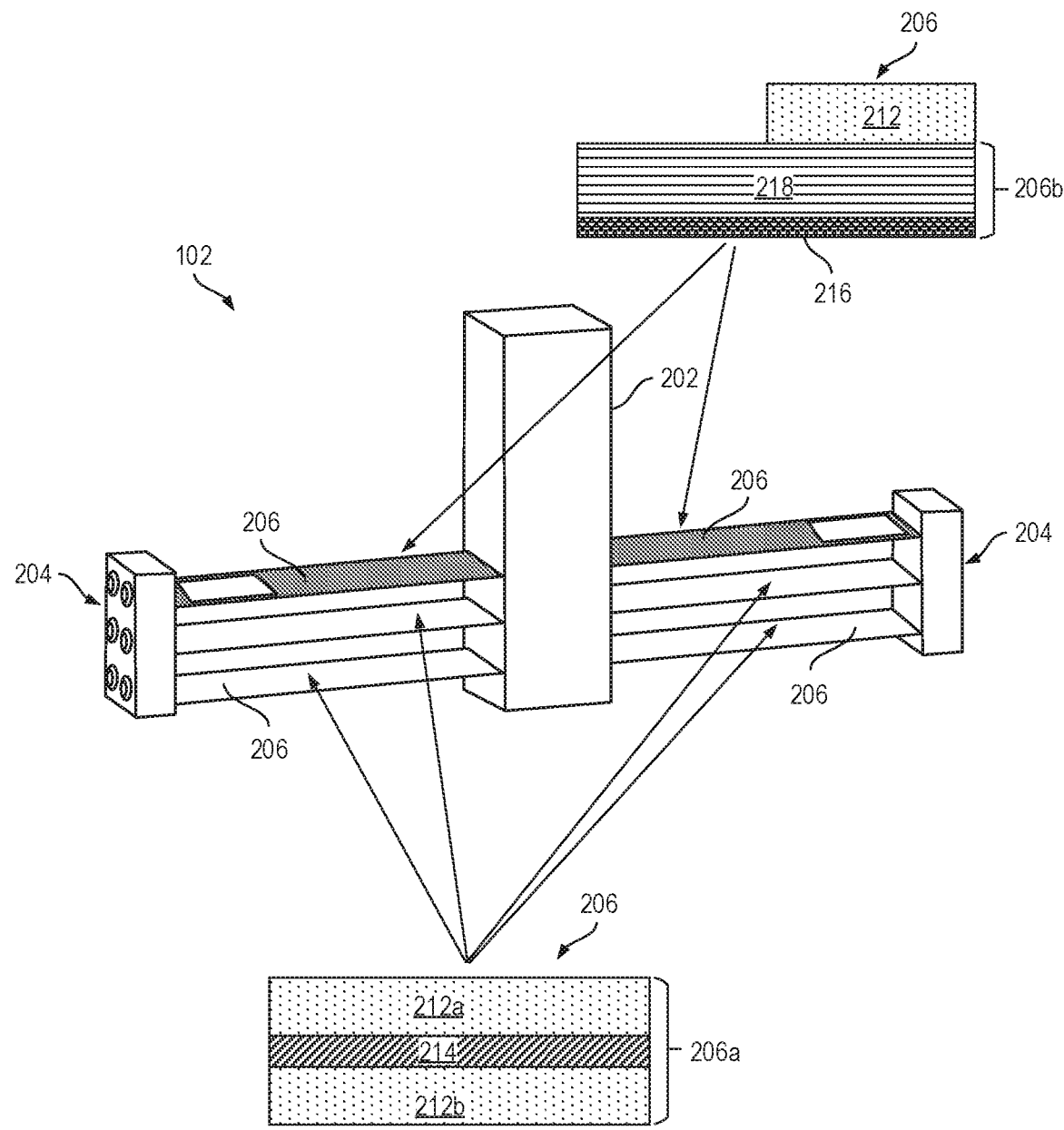
FIG. 6 is a diagrammatic view of the linear actuator for the surgical device, in accordance with a second example embodiment.

As discussed, the linear actuator 102, utilized to power the surgical device 100, is designed to have self-sensing characteristics so as to estimate the displacement of the central rod 202 and/or the individual bending elements 212. The present disclosure provides two alternate design configurations to implement the linear actuator 102 with self-sensing characteristics for the surgical device 100. In a first embodiment, as illustrated in FIG. 5, the linear actuator 102 may employ a mix of 5-layered self-sensing bending actuators 206 with both the actuating portion 206a as well as the sensing portion 206b and 3-layered bending actuators 206' only having the actuating portion 206a. In such configuration, the 3-layered bending actuators 206' are only engaged in actuation while the 5-layered self-sensing bending actuators 206 perform both actuation and sensing tasks. In one example, as illustrated, each bending module 204 may have only one 5-layered self-sensing bending actuators 206 while the rest are 3-layered bending actuators 206'. In a second embodiment, as illustrated in FIG. 6, the linear actuator 102 may employ a mix of 3-layered bending actuators 206' and one or more sensing beams 206". Each sensing beams 206" is constructed by attaching a small patch of piezoelectric material (e.g., PZT-5H) to a base having the sensing element 216. In one implementation of the sensing beam 206", the base forms the sensing portion 206b having a PVDF layer and a Kapton layer. In such configuration, the individual beam elements perform either actuation or sensing. It may be understood that these alternate design configurations for the linear actuator 102 may be helpful to reduce the overall footprint of the linear actuator 102 in the housing 104 and thus in turn allow to add more bending actuators 206 in the linear actuator 102 in view of different applications of the surgical device 100.

Figure 7:
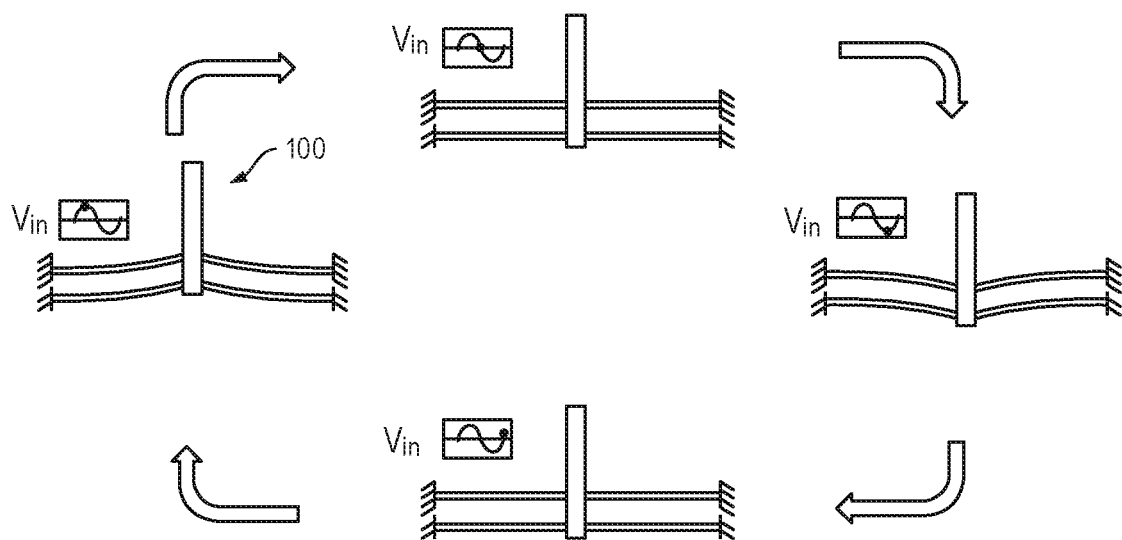
FIG. 7 is a schematic showing the working of the linear actuator, in accordance with an example embodiment.

FIG. 7 illustrates the working of the linear actuator 102 in more detail, in accordance with an example embodiment. As discussed, application of the electric potential results in the deflection of each of the bending actuators 206 in the bending module 204. In an embodiment, the bending actuators 206 in each of the bending modules 204 are wired such that all the bending actuators 206 are electrically connected in parallel and the same electrical signal (voltage) is fed as input to all the bending actuators 206 resulting in a synchronous motion. This results in the tips 222 of each of the bending actuators 206 to move up or down simultaneously in the transverse direction. As illustrated in the cyclical representation of FIG. 7, when a sinusoidal voltage is applied across the bending modules 204, the motion of the central rod 202 is oscillatory corresponding to a current state of the signal. In FIG. 7, the applied voltage signal is denoted by 'Vin', and the dot in the sinusoidal curve represents the current state of the signal. When the dot is shown at peak and trough positions of the sinusoidal curve, correspondingly the central rod 202 is at maximum upward deflection (as shown in 'Position A') and maximum downward deflection (as shown in 'Position C'), respectively. Whereas, when the dot is at base line position of the sinusoidal curve, the central rod 202 is at mean deflection (as shown in 'Position B' and 'Position D'). Therefore, it may be contemplated that the reciprocating movement of the central rod 202, along the transverse direction, may be controlled by the applied voltage in the linear actuator 102.

In some alternate embodiments, the linear actuator 102 may implement a mechanism in which a piezoelectric stack actuator is used as the driving mechanism. A reciprocating blade is used to resect tissues that get lodged in the opening in the outer tube. The stack actuator may be coupled with a fluid amplification mechanism to increase its displacement. In yet another alternate embodiment, the linear actuator 102 may implement a mechanism consisting of a magnetostrictive actuator and an end effector consisting of a fixed bar and a sliding bar. When the magnetostrictive actuator is actuated, the sliding bar moves forward and any tissues in the notch are pinched and severed from the surrounding tissues. Fluid amplification may be used for increasing the amplitude of the magnetostrictive actuator.

Referring back to FIG. 1, the housing 104 of the surgical device 100 is shown to have a generally rectangular shape; however, it may be contemplated that the housing 104 may have any other suitable shape so as to properly accommodate the linear actuator 102 and other components therein. In some examples, the housing 104 of the surgical device 100 is fabricated using 3D printing techniques, such as fused deposition modeling and is composed of thermoplastic polymers, such as ABS (Acrylonitrile butadiene styrene) plastic as the material. However, it may be contemplated that the housing 104 may be manufactured using a variety of fabrication techniques including, but not limited to, molding, pressing, etc.; and further be manufactured from a variety of materials including, but not limited to, stainless steel, hard rubber, etc.

As illustrated in FIG. 1, the housing 104 provides a mouth 110 in the form of an opening which is located along one of long edges thereof. The mouth 110 is open to the outside of the housing 104 so as to allow the cutting mechanism 106 to extend into the housing 104 and be connected to the linear actuator 102 therefrom. In an embodiment, the housing 104 may provide slots 112 formed in a base 114 thereof. In one example, the slots 112 may be extending parallel to the long edge of the rectangular housing 104. The linear actuator 102 may be arranged on the slots 112 such that the linear actuator 102 may be able to traverse along the length of the slots 112 in either direction. For this purpose, the linear actuator 102 may be coupled to the slots 112 from a bottom side thereof, via one or a combination of hex nuts, pan head screws and the like. In particular, the linear actuator 102 may be coupled to the housing 104 at the support bodies 208 of the various bending modules 204, so as to allow for the bending movement of the bending actuators 206 in each of the bending module 204. It may be understood that such arrangement with slots 112 may help to adjust the position of the linear actuator 102 inside the housing 104, and thereby allow to accommodate linear actuators of varying sizes and shapes inside the housing 104 without the need of modifying the housing 104. In some examples, the housing 104 may also provide another set of slots (not shown) formed perpendicular to the existing slots 112, so as to allow the linear actuator 102 to traverse along a direction parallel to a short edge of the housing 104, if required.

It shall be noted that the linear actuator 102 of the present disclosure is a scalable linear actuator as the number of the bending modules 204, or alternatively the number of the bending actuators 206 in each of the bending module 204 may be modified to scale the force output of the linear actuator 102, for example to match the required force output for an application of the surgical device 100. As may be understood that the resultant force produced at the central rod 202 is calculated by summing the contributions of all the individual bending modules 204 coupled thereto, in the linear actuator 102; and therefore, higher the number of the bending modules 204 and/or the bending actuators 206, larger will be the force generated by the linear actuator 102. Further, it may be understood that it may be possible to vary the displacement output of the linear actuator 102 by modifying its geometric and/or material parameters, e.g. by increasing or decreasing the length of the bending actuators 206 within the design constrains.

In the present configuration, the housing 104 is designed to conveniently adjust or even entirely replace the linear actuator 102 to allow for scalability. For instance, the housing 104, by means of the slots 112, allows to adjust the linear actuator 102 therein, so that linear actuators of varying length may accommodate within the housing 104 without any modification thereto. Further, the housing 104 is designed to conveniently remove the linear actuator 102 by simply taking out the fasteners. This enables to employ linear actuators with different numbers and/or configurations of the bending modules 204 therein, and consequently allows to scale the force output as may be required for different applications of the surgical device 100. Further, the housing 104 is designed so that the central rod 202, acting as the end effector in the linear actuator 102, may be conveniently attached to the cutting mechanism 106 for transferring reciprocating motion. In some examples, the bending modules 204 of the linear actuator 102 may be separated by spacers inside the housing 104. Further, in some examples, the bending modules 204 may be clamped to the housing 104 and the clamping force may be adjusted by a screw arrangement (not shown) provided in the housing 104 in order to achieve proper bending movement of the bending modules 204, in the linear actuator 102.

As discussed, the housing 104 may be a generally rectangular box shaped structure. In one example embodiment, the housing 104 may have dimensions of about 135 mm along the long edge and 50 mm along the short edge. Further, the linear actuator 102 therein may be about 100 mm in length parallel along the long edge of the housing 104. In such configuration, the slots 112 in the housing 104 may allow the surgical device 100 to be used for linear actuators having the bending actuators ranging from 25 mm to 50 mm in length. In one example, the sinusoidal voltage input used for actuation of the linear actuator 102 may have a maximum amplitude of about 190 V and the resonant frequency of the linear actuator 102 is about 135 Hz for the geometry and materials considered for the surgical device 100. Further, in one example, the handle 108 may have dimensions of about 45 mm in width and about 25 mm in thickness. Also, the handle 108 may have a suitable length extending from the base 114 of the housing 104 so as to allow for convenient gripping for manual use, and also allow the surgical device 100 to be attached to a mounting of a surgical robot or for testing purposes. In some examples, the surgical device 100 may include driving electronics, other relevant circuitry and one or more batteries (not shown) provided inside the handle 108 in order to provide electric power to the linear actuator 102 for generating reciprocating movement. Further, in some examples, the surgical device 100 may have a power inlet (not shown) provided at the handle 108 either to charge the batteries or to directly power the linear actuator 102, as required.

Figure 8:
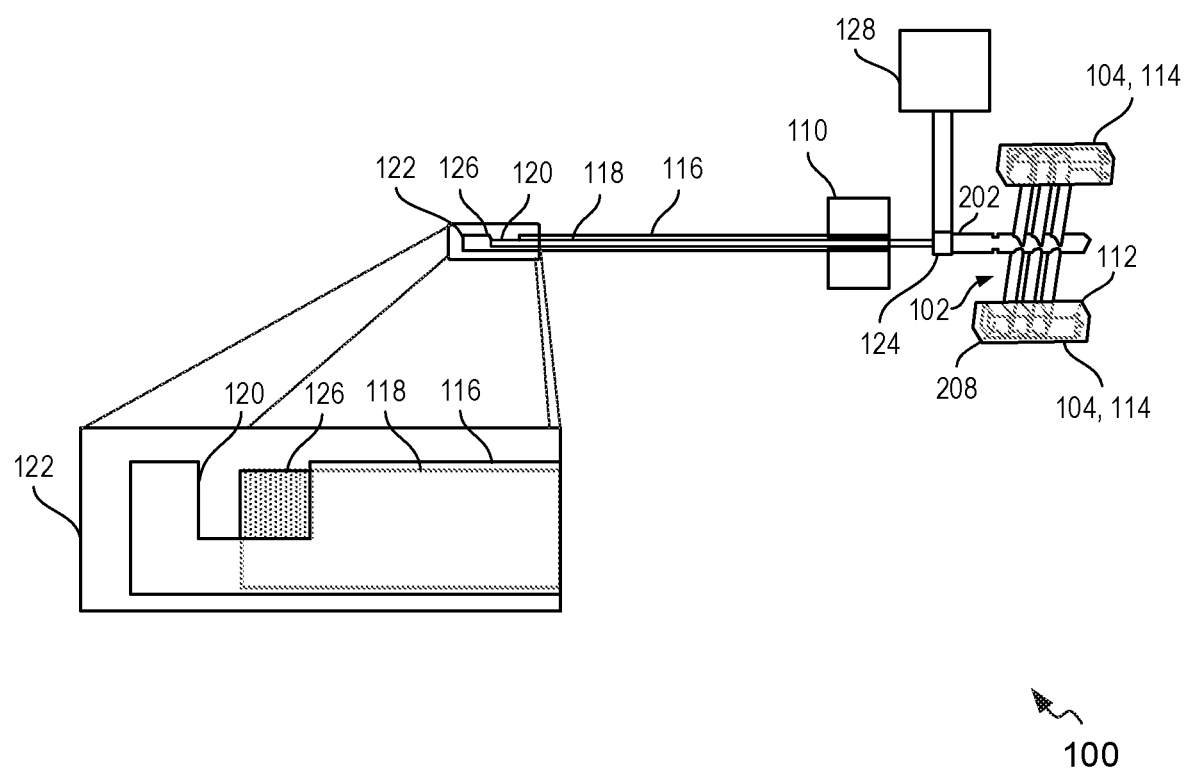
FIG. 8 is a schematic representation of the surgical device, in accordance with an example embodiment.

Moving on, FIG. 8 illustrates a simplified representation of the surgical device 100 of the present disclosure. As illustrated, the cutting mechanism 106 of the present surgical device 100 includes two concentric tubes, an outer tube 116 and an inner tube 118. In the present design, the outer tube 116 is rigidly connected to the housing 104, in the surgical device 100. In particular, the outer tube 116 is connected to the mouth 110 of the housing 104. The outer tube 116 has a notch 120 formed at a distal end 122 thereof. While, in the illustration, the notch 120 is shown to have a uniform rectangular design; in other examples, the notch 120 may have a tapered design without any limitations. Further, the inner tube 118 is connected to the linear actuator 102 via a coupling 124 (e.g. a flange coupling), and moves in a linear reciprocating motion along therewith. Further, a tip 126 of the inner tube 118 overlaps with the notch 120 in the outer tube 116. The lengths of the two concentric 116, 118 may be varied as long as the tip 126 of the inner tube 118 coincides with the location of the notch 120 in the outer tube 116. Further, the diameters of the two tubes 116, 118 may also be variable and chosen based on the applications of the surgical device 100, such as, for example, constraints imposed by a particular incision or opening size in surgery. In the present configuration of the surgical device 100, the outer tube 116 has a diameter of about 2.1 mm and the inner tube 118 has a diameter of about 1.7 mm; while the length of the outer tube 116 is about 120 mm and the length of the inner tube 118 is about 130 mm. In one example, the two tubes 116, 118 are made of materials that are generally rigid, such as rigid plastics or metal. Further, in one example, the two tubes 116, 118 are constructed of stainless steel, and more preferably, 304SS grade steel typically used in medical instruments.

In the cutting mechanism 106, the position of the outer tube 116 remains fixed, i.e., the outer tube 116 is not translatable along the direction of longitudinal axis with respect to housing 104. Whereas, the inner tube 118 reciprocates by virtue of being connected to the control rod 202 of the linear actuator 102. Therefore, the inner tube 118 moves relative to the outer tube 116 in the cutting mechanism 106. It may be contemplated by a person skilled in the art that such relative reciprocating movement may cause a shear effect which may be utilized for cutting of any object present in the notch 120. To this effect, in accordance with an embodiment of the present disclosure, the surgical device 100 may be implemented as a tissue resection device using the relative motion between the outer tube 116 and the inner tube 118 to perform cutting action.

In one embodiment, the surgical device 100 may include an aspiration mechanism (generally represented by the block with numeral 128 in FIG. 8) connected to the cutting mechanism 106. In particular, the aspiration mechanism 128 may include a vacuum source to generate vacuum inside the region between the outer tube 116 and the inner tube 118 in order to suck tissues in vicinity of the distal end 122 of the outer tube 116 into the notch 120. Once inside the notch 120, the tissues are then resected by the tip 126 of the inner tube 118 moving through the notch 120. In some examples, the aspiration mechanism 128 may also include an aspiration tube connected to the cutting mechanism 106 to aspirate the chopped tissues and debris. The aspiration mechanism 128 may further include an electric pump to aspirate the debris to a collection jar away from the surgical device 100.

Figure 9:
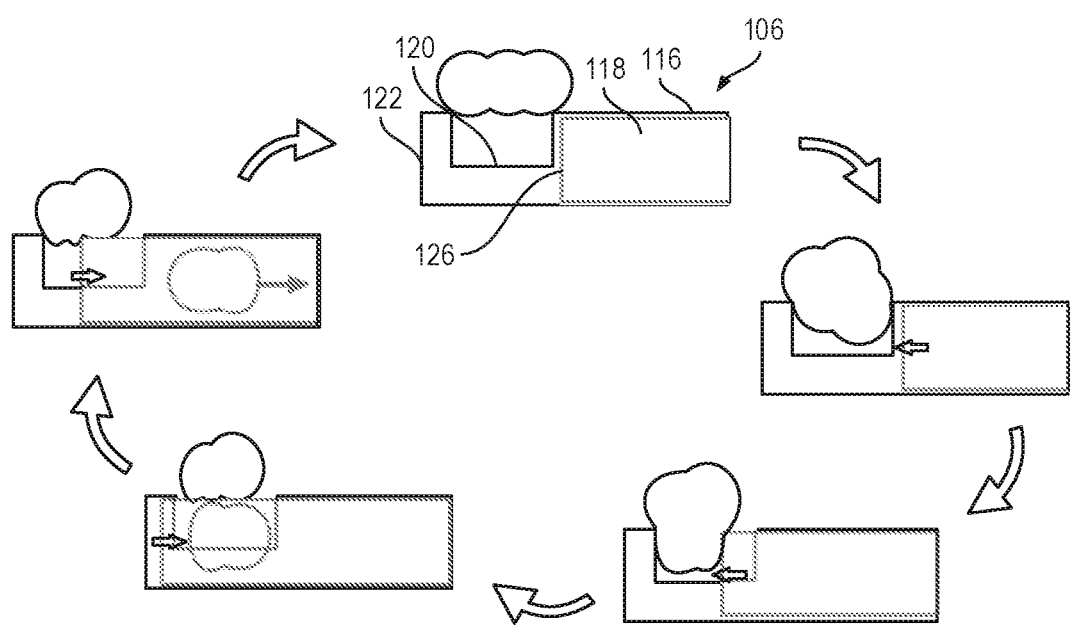
FIG. 9 is a schematic showing the working of the surgical device, in accordance with an example embodiment.

FIG. 9 illustrates the functioning of the surgical device 100 for tissue resection. As seen in step 'a', the surgical device 100 may be activated and directed towards a tissue mass to be removed by a surgeon such that the distal end 122 of the outer tube 116 is in vicinity of the tissue mass. As seen in step 'b', the tissue mass is sucked into the notch 120 (by the aspiration mechanism 128). Next, as seen in step 'c', the inner tube 118 by virtue of its reciprocating motion may move towards the tissue mass collected in the notch 120. Next, as seen in step 'd', the inner tube 118 moves through the notch 120 and the collected tissue mass may get resected by the inner tube 118. Finally, as seen in step 'e', the resected tissue is aspirated (by the aspiration mechanism 128) and more tissue mass is sucked into the notch 120 for further processing.

Tissue resection and removal is a major component of minimally invasive surgical (MIS) procedures. It may be contemplated that increasing the resection speed of surgical devices involved in this task would result in reduction of the overall duration of the surgery. However, increasing the resection speed and maintaining a high precision in cutting target tissues without damaging surrounding tissues is a challenge. Conventional devices like graspers, scalpels and surgical blades are limited by the speed and dexterity of the surgeon. For repetitive tasks such as tissue ablation and resection, powered surgical devices can play a pivotal role in improving not only in patient comfort and surgical outcomes but also reduce fatigue for surgeons and reduce surgery times. Further, it is known that haptic feedback greatly improves surgeon's outcomes in surgeries. Sensing tissue stiffness is one aspect of haptic feedback and can enable an operator or surgeon to distinguish between tissues of various kinds or between a tissue and a tumor. The stiffness or human tissues varies widely over orders of magnitude ranging from a few kilopascals to a few megapascals. To differentiate various tissues a sensor needs to be used to estimate the tissue stiffness. Conventional surgical devices use a standalone stiffness sensor in their measurements. For use in a practical setting, these sensors need to be packaged and assembled in a housing. The housing assembly and any other mechanical force transduction mechanisms can affect sensor dynamics and the obtained results. Therefore, it would be convenient if a single device could perform the task of cutting tissues as well sensing tissue's stiffness.

The present surgical device 100 integrates actuation and sensing into one device making it easier for the surgeon to perform both tasks without the need of swapping devices during surgical procedure. In one example, the present surgical device 100 can distinguish between tissues of varying stiffness. This would be helpful to distinguish between a harder and softer tissue in-situ during the surgery without the need for a separate device. This could be additionally useful where the field of view through endoscopic camera gets obstructed by blood and/or other fluids during a surgical procedure. This also paves the path for automation where this self-sensing characteristics can be extended and enhanced by incorporating a feedback loop to terminate the resection at the tip automatically when it detects tissues of a stiffness other than that specified by the operator. For example, this can be used to resect stiffer tumor tissues selectively without damaging the surrounding healthy tissues.

Furthermore, conventional surgical devices employing a linear actuator consisting of a DC motor and a cam arrangement for converting the rotational motion to a linear motion, are generally inefficient. The present surgical device 100 with self-sensing piezoelectric linear actuator 102 can replace the DC motor plus cam linear actuation mechanism with added benefits of virtually zero friction, higher bandwidth and self-sensing capabilities. It is known that different kinds of tissues have different optimum cutting frequencies. The higher bandwidth of the present linear actuator 102 could be used to tune the frequency of the surgical device 100 for a particular kind of tissue while the self-sensing capability could be leveraged to distinguish between different tissue types in-situ and prevent accidental damage to healthy tissues.

In the surgical device 100, the linear actuator 102 is employed to power the reciprocating forms of the cutting mechanism 106. As discussed, the linear actuator 102 includes multiple piezoelectric bending elements 204 arranged symmetrically around the central rod 202 that acts as the end-effector. The present design of the surgical device 100 provides that the various bending elements 204 that comprise the linear actuator 102 may be conveniently swapped, added or removed depending on the demands of the application for the surgical device 100. This aspect improves the serviceability and re-usability of the present surgical device 100.

Embodiments of the present disclosure substantially eliminate or at least partially address the aforementioned problems in the background, and provide an improved surgical device. The present surgical device 100 has self-sensing capabilities which enable it to differentiate between tissues of different stiffness values in-situ and prevent accidental damage to healthy tissues during surgical procedures. The surgical device 100 using the piezoelectric based linear actuator 102 is further configured to generate high force output and high displacement which enables the present surgical device 100 to be implemented for varying surgical procedures. Furthermore, the present surgical device 100 provides added advantage of compact size, high bandwidth, low power consumption, among others.

The embodiments illustrated and described herein as well as embodiments not specifically described herein but within the scope of aspects of the invention constitute exemplary surgical device.

The benefits and advantages described above may relate to one embodiment or may relate to several embodiments. The embodiments are not limited to those that solve any or all of the stated problems or those that have any or all of the stated benefits and advantages.

The above description is given by way of example only and various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

What is claimed is:

1. A surgical device, comprising:
   a housing;
   a linear actuator disposed in the housing, the linear actuator comprising:
      a central rod; and
      one or more bending modules connected to the central rod, each of the one or more bending modules comprising one or more bending actuators, each of the one or more bending actuators comprising one or more layers of piezoelectric bending elements configured to provide a reciprocating movement to the central rod upon applying a voltage, wherein each of the one or more bending actuators comprises a metallic layer disposed between at least two layers of bending elements; and
   a cutting mechanism coupled to the central rod.

2. The surgical device as claimed in claim 1, wherein each of the one or more bending actuators comprises an insulating layer disposed on one of at least two layers of bending elements.

3. The surgical device as claimed in claim 2, wherein each of the one or more bending actuators comprises a sensing element disposed on the insulating layer.

4. The surgical device as claimed in claim 1, wherein each of the one or more bending modules comprises one or more sensing beams.

5. The surgical device as claimed in claim 1, wherein the cutting mechanism comprises an outer tube fixedly connected to the housing and an inner tube coupled to the central rod to receive the reciprocating movement therefrom.

6. The surgical device as claimed in claim 5, wherein the outer tube and the inner tube are concentric tubes.

7. The surgical device as claimed in claim 6, wherein the outer tube provides a notch formed at a distal end thereof, and wherein the inner tube is configured to reciprocate within the outer tube to move through the notch.

8. A surgical device, comprising:
   a housing;
   a linear actuator disposed in the housing, the linear actuator comprising:
      a central rod; and
      one or more bending modules connected to the central rod, each of the one or more bending modules comprising one or more bending actuators, at least one of the one or more bending actuators comprising:
         at least two layers of bending elements; and
         a metallic layer disposed between each of the at least two layers of bending elements; and
   a cutting mechanism coupled to the central rod.

9. The surgical device as claimed in claim 8, wherein at least one of the one or more bending actuators comprises:
   an insulating layer disposed on one of the at least two layers of bending elements; and
   a sensing element disposed on the insulating layer.

10. The surgical device as claimed in claim 9, wherein the insulating layer is composed of a polyimide material.

11. The surgical device as claimed in claim 10, wherein the polyimide material is Kapton.

12. The surgical device as claimed in claim 9, wherein the sensing element is constructed of one of more of polyvinylidene fluoride and polyvinylidene difluoride (PVDF) material.

13. The surgical device as claimed in claim 8, wherein the one or more bending modules are arranged coaxially about the central rod.

14. The surgical device as claimed in claim 13, wherein the one or more bending modules are arranged equidistant to each other about the central rod.

15. The surgical device as claimed in claim 8, wherein the one or more bending modules are disposed orthogonal to the central rod.

16. The surgical device as claimed in claim 8, wherein each of the at least two layers of bending elements is a piezoelectric bending element.

17. The surgical device as claimed in claim 14, wherein each of the at least two layers of bending elements is constructed of PZT-5H material.

18. The surgical device as claimed in claim 8, wherein the metallic layer is composed of brass material.

* * * * *